(12) United States Patent
Horton, III et al.

(10) Patent No.: US 6,558,410 B1
(45) Date of Patent: May 6, 2003

(54) CARDIAC DEBLOCKING DEVICE AND METHOD

(75) Inventors: Isaac B. Horton, III, Raleigh, NC (US); Kurt Anthony Garrett, Raleigh, NC (US)

(73) Assignee: RemoteLight, Inc., Raleigh, NC (US)

( * ) Notice: Subject to any disclaimer, the term of this patent is extended or adjusted under 35 U.S.C. 154(b) by 101 days.

(21) Appl. No.: 09/724,068

(22) Filed: Nov. 28, 2000

(51) Int. Cl.$^7$ ............................................... A61H 33/00
(52) U.S. Cl. ....................................................... 607/85
(58) Field of Search ............................. 604/88, 89, 90, 604/91, 92, 93, 94, 95; 602/2; 606/1, 2, 3, 4, 5, 6, 7, 8, 9, 10, 11, 170; 600/101, 102, 108; 106/43; 502/350

(56) References Cited

U.S. PATENT DOCUMENTS

| | | | | |
|---|---|---|---|---|
| 4,830,460 A | * | 5/1989 | Goldenberg | 385/118 |
| 5,042,494 A | * | 8/1991 | Alfano | 600/477 |
| 5,112,328 A | * | 5/1992 | Taboada et al. | 128/898 |
| 5,836,905 A | * | 11/1998 | Lemelson et al. | 604/101.05 |
| 5,938,680 A | * | 8/1999 | Ginn | 606/190 |
| 5,947,894 A | * | 9/1999 | Chapman et al. | 128/857 |
| 6,027,766 A | | 2/2000 | Greenberg et al. | |
| 6,039,728 A | * | 3/2000 | Berlien et al. | 606/15 |
| 6,055,977 A | * | 5/2000 | Linard | 126/200 |
| 6,056,746 A | * | 5/2000 | Goble et al. | 606/41 |
| 6,095,149 A | * | 8/2000 | Sharkey et al. | 128/898 |
| 6,103,363 A | | 8/2000 | Boire et al. | |
| 6,110,528 A | | 8/2000 | Kimura et al. | |
| 6,117,337 A | | 9/2000 | Gonzalez-Martin et al. | |
| 6,277,114 B1 | * | 8/2001 | Bullivant et al. | 606/41 |
| 6,296,636 B1 | * | 10/2001 | Cheng et al. | 604/114 |
| 6,306,796 B1 | * | 10/2001 | Suzue et al. | 106/436 |
| 6,309,375 B1 | * | 10/2001 | Glines et al. | 604/187 |
| 6,411,852 B1 | * | 6/2002 | Danek et al. | 128/898 |

* cited by examiner

Primary Examiner—Teresa Walberg
Assistant Examiner—Daniel Richardson
(74) Attorney, Agent, or Firm—Glasgow Law Firm, PLLC

(57) ABSTRACT

A device and method for the surgical removal of tissue from a mammalian body, specifically arteriosclerotic plaques from human beings, including a photo-degradatory endoscope having a tip end and a tubular body connected to a power source, a light source, controls, and a viewer, which are remote from the tip end, the tubular body comprising a light-transmissive material such that catalyst-activating wavelengths emitted from the light source are transmitted to the tip end and through a tip into the body; and a photo-catalyst for tissue degradation that is presented proximal the tip end for making a reaction with catalyst-activating wavelengths transmitted from the light source through the tubular body, through the tip, and into the body.

57 Claims, 2 Drawing Sheets

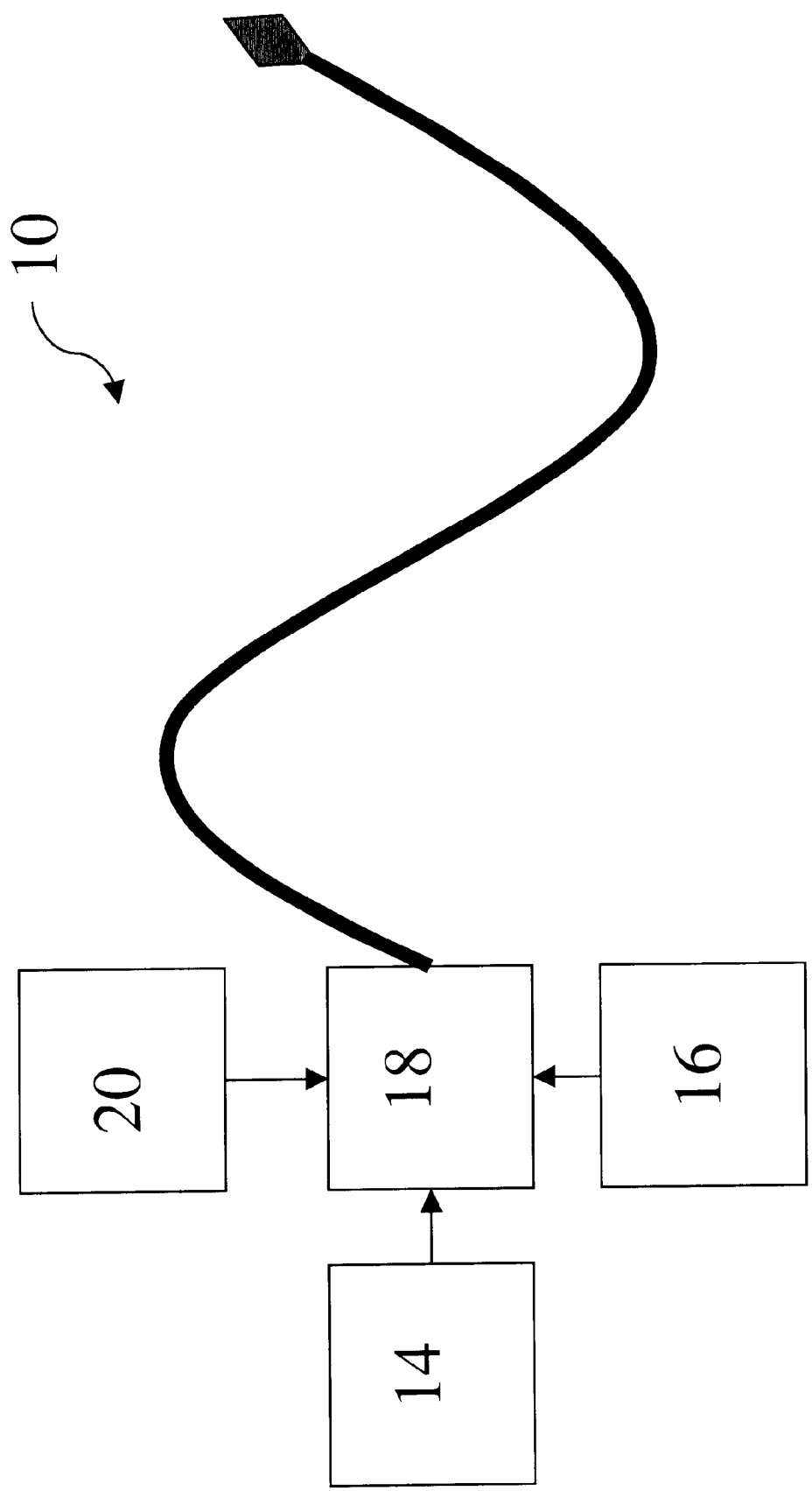

CARDIAC DEBLOCKING DEVICE AND METHOD

BACKGROUND OF THE INVENTION (1) Field of the Invention

The present invention relates generally to a device and method for the surgical removal of tissue from the body and, more particularly, to a device and method for the removal of arteriosclerotic plaques occluding arteries.

(2) Description of the Prior Art

Prevalence and Etiology of Coronary Heart Disease

Coronary heart disease is the leading cause of death among adult males in the United States. Several risk factors have been shown to be involved, including high blood pressure, high blood cholesterol, smoking, obesity, physical inactivity, diabetes, stress, gender, heredity, and age. These factors, in combination, cause damage to the endothelium of blood vessels, the layer of cells lining the interior surface of these vessels. In an attempt to repair the damage to these cells and prevent further damage to the vessel, platelets aggregate at the point of damage, forming clots. These clots, composed of cholesterol and other molecules, gradually harden over time to form large, arteriosclerotic plaques. These plaques may continue to grow, eventually occluding the vessel. If the occlusion occurs in one of the coronary arteries, which supply blood to the heart, the lack of blood results in a life-threatening condition known as cardiac ischemia and the patient may suffer a heart attack.

Prior Art for Treatment of Coronary Heart Disease

A variety of prior art methods and devices were used to restore adequate blood supply to the heart in cases of coronary artery blockage by arteriosclerosis. Replacement of the blocked artery(s) with veins from other regions of the body (coronary by-pass) has been routinely used to restore blood supply to cardiac tissues. Another method involves the introduction of expandable stents into the artery(s), thus holding the artery in an expanded state to and allowing adequate blood supply to the tissue. A third method is the physical removal of the arteriosclerotic plaques by endoscopy-based surgical devices.

However, these methods and devices to ameliorate vessel obstruction have several drawbacks associated with their use. Coronary by-pass procedures are expensive, high-risk, and invasive. In addition, scar tissue may require later surgical procedures to remove additional tissue and/or scar tissue to prevent further blocking and/or damage to the arteries.

Thus, there remains a need for a device to easily, safely, and inexpensively remove obstructing tissue from arteries and other areas of the body.

Titanium Dioxide Self-cleaning Glass

Fouling of glass by oils and other lipids is a problem in certain industries, for example, in analytical chemistry applications. A new technology for cleaning this glass has recently been developed that involves the incorporation of titanium dioxide ($TiO_2$) within the glass. When this glass is irradiated with ultraviolet light, lipids and other hydrocarbons on the exterior surface of the glass spontaneously degrade into the volatile gases methane and ethane, thus leaving no residues on the glass. To date, no medical applications involving this technology are known. The photocatalyst may include photo-activated semiconductors such as Titanium Oxide; $TiO2$ (photo activation wavelength; not more than 388 nm), Tungsten Oxide; $WO2$ (photo activation wavelength; not more than 388 nm), Zinc Oxide; $ZnO$ (photo activation wavelength; not more than 388 nm), Zinc Sulfide; $ZnS$ (photo activation wavelength; not more than 344 nm) and Tin Oxide; $SnO2$ (photo activation wavelength; not more than 326 nm). In addition to these catalysts, other catalysts, such as $PtTiO_2$, are known.

$TiO2$ may be preferably applied as the photocatalyst, considering that the activation power is very high, the catalyst is long-lived with high durability, and safety for human applications is certified, as $TiO2$ has been used safely for a long time in cosmetic and food applications.

SUMMARY OF THE INVENTION

The present invention is directed to a device and method for the surgical removal of tissue from the body.

The present invention is further directed to a method for the removal of tissues from the body by a photo-degradatory endoscope.

In particular, the device and method are directed to the removal of arteriosclerotic plaques that are occluding arteries through the use of a $TiO_2$/glass photo-degradatory endoscope.

Thus, the present invention provides for a device and method to remove tissue, and more specifically arteriosclerotic plaques, from the body.

These and other aspects of the present invention will become apparent to those skilled in the art after a reading of the following description of the preferred embodiment when considered with the drawings.

BRIEF DESCRIPTION OF THE DRAWINGS

FIG. 2 is a schematic diagram of the system according to the present invention.

DETAILED DESCRIPTION OF THE PREFERRED EMBODIMENTS

Figure 1:
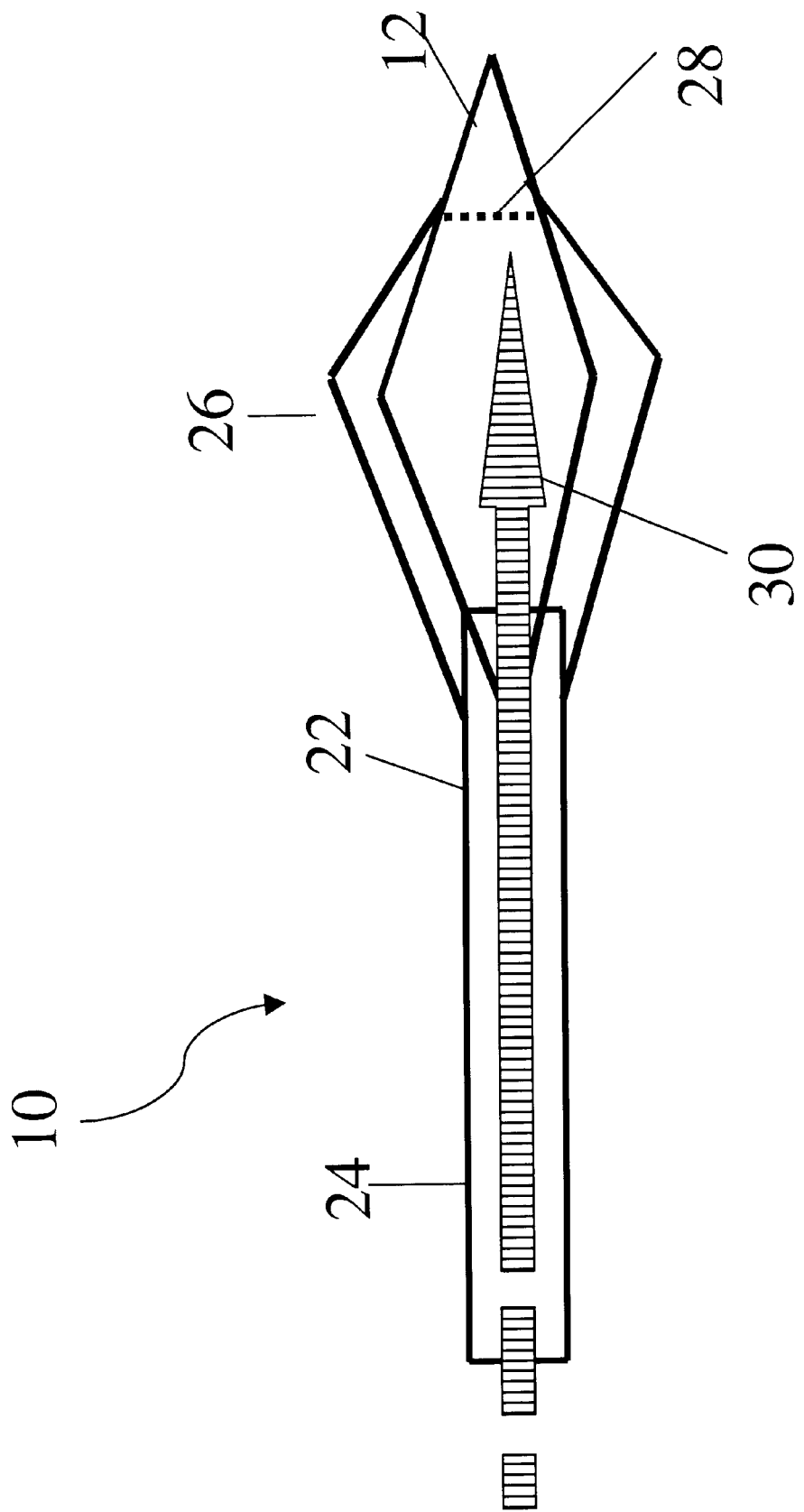
FIG. 1 is a side view of an endoscope constructed according to the present invention.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. As best seen in FIG. 1, the preferred embodiment includes a UV-transmissive endoscope, generally referenced 10, that incorporates a tissue degradatory end tip 12, which is positioned at the remote end 22 of a tubular body 24, which connects the tip and the light source for supplying light 30, and controls, which are connected to the power supply (best seen in FIG. 2). Additionally, the tip 12 preferably includes a shield 26 for shielding the body from UV light emissions at non-targeted tissue regions, particularly as the scope is being introduced to the body and the target area for tissue degradation and/or dissolving. Also preferably, the tip includes a photocatalyst 28, which may be presented as a coating or a film on or proximal to the tip, an integral component of the tip, or as an attachment to the tip. Also, this photocatalyst may be removably attached and disposable. Alternatively, the photocatalyst may be introduced by other means, which are further described in the specification hereinbelow.

As best seen in FIG. 2, the endoscope 10 is connected to a variable power source 14, at least one light source 16, which may include a UV light source and/or a visible light source, controls 18, and a viewer 20. The controls preferably include, but are not limited to, directional controls, focal control, light intensity controls, visible light controls, and on/off power controls. The UV light source and visible light source may be derived from the same lamp system, or may be separate. If derived from the same lamp system, this combined light source may use a UV light filter to block UV light when tissue ablation is not being performed.

Optical components (not shown) may be used to direct, focus, and or otherwise manipulate the UV and visible light, and are preferably, but not exclusively, intended to be positioned between the at least one light source and the tubular body of the endoscope. In general, any of the optical components and also the tubular body of the endoscope, may be made of acrylic or similar materials that degrade over time when exposed to UV light. These components can be replaced when their performance has deteriorated to an unacceptable level.

The catalyst-activating wavelengths rays may be projected downward from a UV light source or a lamp system that includes optical components. These optical components may include, but are not limited to, reflectors, shutters, lenses, splitters, focalizers, mirrors, rigid and flexible light guides, homogenizer or mixing rods, manifolds and other couplers, filters, gratings, diffracters, color wheels, and the like. These optical components are internal to the lamp system and are positioned between the UV light source or lamp and the UV ray light output of the lamp assembly, thereby focusing, directing, and controlling the light ray output that is transmitted through the endoscope.

Additionally, optical component such as gratings, dichroic filters, focalizers, gradient lenses, and off-axis reflectors may be used, as appropriate, for directing and focusing the light through the tubular body and to the target area for tissue degradation.

With regard to lenses, several embodiments are envisioned. Imaging lenses, such as a parabolic lens, and non-imaging lenses, such as gradient lenses, may be used. A gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additonally, more than one reflector may be used with a lamp. For example, dual reflectors or three or more reflectors, as taught in U.S. Pat. Nos. 5,706,376 and 5,862,277, may be incorporated into the preferred embodiment.

The body of the endoscope is tubular and made of UV and visible light-transmissive material. Furthermore, the exterior is coated or otherwise shielded with a UV-opaque material to prevent side emissions of UV light into the body. The tissue degradatory end is made of glass and incorporates $TiO_2$ in the glass or other catalyst-compatible material. Catalyst-activating wavelengths directed through the endoscope irradiate the $TiO_2$. When irradiated with catalyst-activating wavelengths, such a device catalytically decomposes lipids and other organic compounds in contact with the tip. Damage to proximal non-targeted tissue is prevent through the use of a shield that surrounds the active surfaces of the tip end that are not used for targeted tissue degradation.

In the preferred embodiment, the endoscope is directed into the body through a vein or artery to the site of operation. At the site of operation, the tip is juxtaposed to the tissue to be ablated, and catalyst-activating wavelengths are directed through the endoscope. When the catalyst-activating wavelengths irradiate the $TiO_2$ tip, fatty acids and other organic molecules are degraded and the tissue is ablated.

Alternatively to being incorporated in the tip, the $TiO_2$ or other photocatalyst may be delivered to the site of operation independent of the tissue-degradatory endoscope. For example, glass beads containing the $TiO_2$ or other catalyst may be injected into the body at the site of operation or distal to the site of operation. The tissue-degradatory endoscope is then directed to the site of operation. When catalyst-activating wavelengths are shown through the endoscope, they strikes the catalyst in the area of the tissue to be ablated, thus ablating the tissue. Numerous means of delivering the catalyst are envisioned, including, but not limited to, local or distal intravenous (i.v.), intramuscular (i.m.) or other means of injection, and endoscopic delivery by the photodegradatory endoscope or other endoscope.

Certain modifications and improvements will occur to those skilled in the art upon a reading of the foregoing description. By way of example, the endoscope may be constructed of a variety of materials, including titanium or plastic. Additionally, other components, particularly sensors, may be included with the endoscope. All modifications and improvements have been deleted herein for the sake of conciseness and readability but are properly within the scope of the following claims.

We claim:

1. A device for the surgical removal of tissue from a mammalian body comprising a photo-degradatory endoscope having a tip end, the tip end further including a photocatalyst for tissue degradation, and a tubular body connected to a power source, at least one light source, controls, and a viewer, which are remote from the tip end, the tubular body comprising a UV-transmissive material such that UV emissions from the at least one light source are transmitted to the tip end and through a tip into the mammalian body.

2. The device according to claim 1, wherein the endoscope further includes a photocatalyst for tissue degradation.

3. The device according to claim 1, wherein the photocatalyst is incorporated into the tip thereby providing a catalytic reaction in proximity to the tip inside the body.

4. The device according to claim 1, wherein the photocatalyst is located proximal to but not incorporated into the tip thereby providing a catalytic reaction in proximity to the tip inside the body.

5. The device according to claim 1, wherein the photocatalyst is provided into the body via oral administration.

6. The device according to claim 1, wherein the photocatalyst is provided into the body via intravenous administration.

7. The device according to claim 1, wherein the photocatalyst is provided into the body via injection.

8. The device according to claim 1, wherein the photocatalyst is provided into the body via intramuscular injection.

9. The device according to claim 1, wherein the photocatalyst is released from the endoscope at a site within the body.

10. The device according to claim 1, wherein the photocatalyst is presented in a coating proximal to the tip.

11. The device according to claim 1, wherein the photocatalyst is presented in a film proximal to the tip.

12. The device according to claim 1, wherein the photocatalyst is integrated into the tip and sealed from direct exposure to the body.

13. The device according to claim 1, wherein the photocatalyst is embedded into the tip and sealed from direct exposure to the body.

14. The device according to claim 1, wherein the photocatalyst is selected from the consisting of TiO2, WO2, ZnO, ZnS, SnO2, and $PtTiO_2$ and the like.

15. The device according to claim 1, further including at least one optical component positioned between the at least one light source and the tubular body.

16. The device according to claim 1, wherein the at least one optical component is selected from the group consisting of reflectors, shutters, lenses, splitters, focalizers, mirrors, rigid and flexible light guides, homogenizer, mixing rods, manifolds and other couplers, filters, gratings, diffracters, and color wheels.

17. The device according to claim 1, wherein the tubular body includes fiber optic transmission lines.

18. The device according to claim 1, wherein the at least one light source includes a UV light source.

19. The device according to claim 1, wherein the at least one light source includes a visible light source.

20. The device according to claim 1, wherein the at least one light source is a single UV light source.

21. The device according to claim 1, wherein the endoscope is phototransmissive.

22. The device according to claim 1, wherein the endoscope comprises glass.

23. The device according to claim 1, wherein the endoscope comprises plastic.

24. The device according to claim 1, wherein the endoscope comprises an acrylic material.

25. The device according to claim 1, wherein the endoscope comprises a ceramic material.

26. The device according to claim 1, wherein the endoscope comprises a vitreoceramic material.

27. The device according to claim 1, wherein the tissue is arteriosclerotic plaques that are occluding arteries.

28. The device according to claim 1, wherein the power supply and controls provide for variable power.

29. The device according to claim 1, further including a shield surrounding active surfaces of the tip end that are not used for tissue degradation.

30. A device for the surgical removal of tissue from a mammalian body comprising
a photo-degradatory endoscope having a tip end and a tubular body connected to a power source, a light source, controls, and a viewer, which are remote from the tip end, the tubular body comprising a UV-transmissive material such that UV emissions from the light source are transmitted to the tip end and through a tip into the body; and a photocatalyst for tissue degradation that is presented proximal the tip end for making a reaction with UV emissions transmitted from the light source through the tubular body, through the tip, and into the mammalian body.

31. The device according to claim 30, wherein the photocatalyst is incorporated into the tip thereby providing a catalytic reaction in proximity to the tip inside the body.

32. The device according to claim 30, wherein the photocatalyst is located proximal to but not incorporated into the tip thereby providing a catalytic reaction in proximity to the tip inside the body.

33. The device according to claim 30, wherein the photocatalyst is provided into the body via oral administration.

34. The device according to claim 30, wherein the photocatalyst is provided into the body via intravenous administration.

35. The device according to claim 30, wherein the photocatalyst is provided into the body via injection.

36. The device according to claim 30, wherein the photocatalyst is provided into the body via intramuscular injection.

37. The device according to claim 30, wherein the photocatalyst is released from the endoscope at a site within the body.

38. The device according to claim 30, wherein the photocatalyst is presented in a coating proximal to the tip.

39. The device according to claim 30, wherein the photocatalyst is presented in a film proximal to the tip.

40. The device according to claim 30, wherein the photocatalyst is integrated into the tip and sealed from direct exposure to the body.

41. The device according to claim 30, wherein the photocatalyst is embedded into the tip and sealed from direct exposure to the body.

42. The device according to claim 30, wherein the photocatalyst is selected from the group consisting of TiO2, WO2, ZnO, ZnS, SnO2, and $PtTiO_2$ and the like.

43. The device according to claim 30, further including at least one optical component positioned between the light source and the tubular body.

44. The device according to claim 30, wherein the at least one optical component is selected from the group consisting of reflectors, shutters, lenses, splitters, focalizers, mirrors, rigid and flexible light guides, homogenizer, mixing rods, manifolds and other couplers, filters, gratings, diffracters, and color wheels.

45. The device according to claim 30, wherein the tubular body includes fiber optic transmission lines.

46. The device according to claim 30, wherein the endoscope is phototransmissive.

47. The device according to claim 30, wherein the endoscope comprises glass.

48. The device according to claim 30, wherein the endoscope comprises plastic.

49. The device according to claim 30, wherein the endoscope comprises an acrylic material.

50. The device according to claim 30, wherein the endoscope comprises a ceramic material.

51. The device according to claim 30, wherein the endoscope comprises a vitreoceramic material.

52. The device according to claim 30, wherein the tissue is arteriosclerotic plaques that are occluding arteries.

53. The device according to claim 30, wherein the power supply and controls provide for variable power.

54. The device according to claim 30, wherein the light source is a UV light source.

55. The device according to claim 30, further including a shield surrounding active surfaces of the tip end that are not used for tissue degradation.

56. A method for the surgical removal of tissue from a mammalian body comprising the steps of:
   providing a photo-degradatory endoscope having a tip end and a tubular body connected to a power source, at least one light source, controls, and a viewer, which are remote from the tip end, the tubular body comprising a UV-transmissive material such that UV emissions from the at least one light source are transmitted to the tip end and through a tip into the mammalian body; and
   introducing a photocatalyst for tissue degradation that is presented proximal the tip end for making a reaction with UV emissions transmitted from the light source through the tubular body, through the tip, and into the mammalian body;
   inserting the endoscope into the mammalian body;
   activate the light source;
   stimulate the catalyst with catalyst-activating wavelengths emissions;
   produce a reaction that degrades the tissue;
   deactivate the light source; and
   remove the endoscope from the mammalian body.

57. The method according to claim 56, wherein the photocatalyst is incorporated into the tip thereby providing a catalytic reaction in proximity to the tip inside the mammalian body.

\* \* \* \* \*